United States Patent
Schilling

(10) Patent No.: US 11,616,397 B2
(45) Date of Patent: Mar. 28, 2023

(54) MAGNETIC ALIGNMENT OF TRANSCUTANEOUS ENERGY TRANSFER COILS

(71) Applicant: Medtronic, Inc., Minneapolis, MN (US)

(72) Inventor: Eric A. Schilling, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/369,259

(22) Filed: Jul. 7, 2021

(65) Prior Publication Data
US 2022/0052553 A1    Feb. 17, 2022

Related U.S. Application Data

(60) Provisional application No. 63/064,668, filed on Aug. 12, 2020.

(51) Int. Cl.
| | | |
|---|---|---|
| *H02J 50/10* | (2016.01) | |
| *H01F 38/14* | (2006.01) | |
| *H01F 27/24* | (2006.01) | |
| *A61M 60/178* | (2021.01) | |
| *A61M 60/875* | (2021.01) | |

(52) U.S. Cl.
CPC .............. *H02J 50/10* (2016.02); *H01F 27/24* (2013.01); *H01F 38/14* (2013.01); *A61M 60/178* (2021.01); *A61M 60/875* (2021.01)

(58) Field of Classification Search
CPC .... H02J 50/10; H02J 7/00034; H02J 2310/23; H02J 50/12; H01F 27/24; H01F 38/14; A61M 60/178; A61M 60/875; A61M 60/216; H04B 5/0037; H04B 5/0081; A61N 1/3787; A61N 1/37229
See application file for complete search history.

(56) References Cited

U.S. PATENT DOCUMENTS

| | | | |
|---|---|---|---|
| 8,265,770 B2 | 9/2012 | Toy et al. | |
| 8,634,909 B2 * | 1/2014 | Zimmerling | ......... A61N 1/3718 607/116 |

(Continued)

FOREIGN PATENT DOCUMENTS

| | | |
|---|---|---|
| EP | 2548612 A1 | 1/2013 |
| WO | 2009/023905 A1 | 2/2009 |

(Continued)

OTHER PUBLICATIONS

International Search Report and Written Opinion of International Application No. PCT/US2021/041925, dated Oct. 22, 2021, 9 pp.

(Continued)

*Primary Examiner* — Pinping Sun
(74) *Attorney, Agent, or Firm* — Shumaker & Sieffert, P.A.

(57) ABSTRACT

A transcutaneous energy transfer system (TETS) that includes external and internal coils that have permeable cores is provided. According to one aspect, the TETS includes an external coil having disposed in proximity thereto, a first set of at least one permeable core that is wound by windings of the external coil. The TETS also includes an internal coil having disposed in proximity thereto, for each permeable core disposed in proximity to the external coil, a corresponding permeable core that is wound by windings of the internal coil.

23 Claims, 6 Drawing Sheets

(56) References Cited

U.S. PATENT DOCUMENTS

| | | | | |
|---|---|---|---|---|
| 8,702,599 | B2* | 4/2014 | De Domenico | A61B 1/267 600/194 |
| 9,375,567 | B2* | 6/2016 | Fell | H02J 7/025 |
| 2002/0032471 | A1* | 3/2002 | Loftin | A61N 1/37276 333/32 |
| 2012/0265003 | A1* | 10/2012 | D'Ambrosio | A61N 1/3787 600/16 |
| 2014/0043127 | A1* | 2/2014 | Worek | H01F 27/38 336/178 |
| 2015/0034842 | A1* | 2/2015 | Uchida | H01J 37/20 335/219 |
| 2016/0285319 | A1* | 9/2016 | Maniktala | H02J 50/40 |
| 2017/0005525 | A1* | 1/2017 | Lecias | H02J 5/005 |
| 2018/0198325 | A1* | 7/2018 | Lawrenson | H02J 50/90 |
| 2018/0254150 | A1* | 9/2018 | Stockman | H01G 4/236 |
| 2019/0006893 | A1* | 1/2019 | Shaw | H02J 50/10 |
| 2019/0043660 | A1* | 2/2019 | Jin | H01F 27/346 |
| 2019/0190296 | A1* | 6/2019 | Paralikar | A61M 25/00 |
| 2020/0219643 | A1* | 7/2020 | Li | H02M 7/003 |
| 2020/0289731 | A1* | 9/2020 | Scheffler | A61M 60/462 |
| 2021/0082617 | A1* | 3/2021 | Varghese | H02J 50/10 |

FOREIGN PATENT DOCUMENTS

| | | | | |
|---|---|---|---|---|
| WO | WO-2009023905 A1 * | 2/2009 | | A61N 1/08 |
| WO | WO-2014048433 A1 * | 4/2014 | | A47F 8/00 |

OTHER PUBLICATIONS

Response to Written Opinion dated Oct. 22, 2021, from International Application No. PCT/US2021/041925, filed Dec. 14, 2021, 6 pp.

* cited by examiner

MAGNETIC ALIGNMENT OF TRANSCUTANEOUS ENERGY TRANSFER COILS

CROSS-REFERENCE TO RELATED APPLICATION

This application claims the benefit of U.S. Application Ser. No. 63/064,668, filed Aug. 12, 2020.

FIELD

The present technology is generally related to implantable medical devices such as a left ventricular assist device (LVAD), and more particularly to magnetic alignment of coils for transcutaneous energy transfer.

BACKGROUND

Referring to FIG. 1, an implantable LVAD system 10 has internal components (in the body of the patient) and external components. The LVAD system 10 may typically include an LVAD pump 12 an implanted controller (i-controller) 14 having an internal battery 16, an implanted internal transcutaneous energy transfer system (TETS) coil (i-coil) 18, an external TETS coil (e-coil) 20 and an external power transmitter 21 with a detachable battery 24. In operation, power is supplied from the external power transmitter 21 to the i-controller 14 via mutual coupling of the coils 18 and 20, in order to charge the internal battery 16 of the i-controller 14 and to power the LVAD pump 12. The coils 18 and 20 transfer power by mutual induction of electromagnetic energy over the air and through the body. The power supplied by the external power transmitter 21 may come from the detachable battery 24 or from a wall outlet, for example.

SUMMARY

The techniques of this disclosure generally relate to magnetic alignment of coils for transcutaneous energy transfer. According to one aspect, a transcutaneous energy transfer system (TETS) includes: an external coil having disposed in proximity thereto, a first set of at least one permeable core that is wound by windings of the external coil; and an internal coil having disposed in proximity thereto, for each permeable core disposed in proximity to the external coil, a corresponding permeable core that is wound by windings of the internal coil.

According to one aspect, in some embodiments, the first set of at least one permeable core has a permeable core disposed at a center of the windings of the external coil. In some embodiments, the first set of at least one permeable core has a plurality of permeable cores disposed about a periphery of the external coil.

According to another aspect, a method of manufacture of a transcutaneous energy transfer system (TETS) is provided. The method includes: disposing a first set of at least one permeable core in proximity to an external coil, and winding each of the first set of at least one permeable core by windings of the external coil; and for each permeable core disposed in proximity to the external coil, disposing a corresponding permeable core in proximity to an internal coil, and winding each corresponding permeable core by windings of the internal coil.

According to this aspect, in some embodiments, the method further includes disposing a permeable core at a center of the windings of the external coil. In some embodiments, the method further includes disposing the first set of at least one permeable core about a periphery of the external coil. In some embodiments, the method further includes replacing the at least one permeable core in proximity to the external coil to change an amount of attractive force between the external coil and the internal coil. In some embodiments, the method further includes adjusting an attractive force based on at least one of an implant depth of the internal coil, activity of the patient, and patient comfort. In some embodiments, a design of an attractive force between the external coil and the internal coil is based on characteristics of a population of patients. In some embodiments, the TETS further includes processing circuitry configured to determine a current strength that is at least partially due to alignment between the external coil and the internal coil.

According to another aspect, a TETS is provided that includes an external coil having disposed in proximity thereto, a first set of at least one permeable core that is wound by windings of the external coil; and an internal coil having disposed in proximity thereto, for each permeable core disposed in proximity to the external coil, a corresponding permeable core that is wound by windings of the internal coil.

According to this aspect, in some embodiments, the first set of at least one permeable core includes a permeable core disposed at a center of the windings of the external coil. In some embodiments, a permeable core corresponding to the permeable core disposed at the center of the windings of the external coil is disposed at a center of the windings of the internal coil. In some embodiments, the first set of at least one permeable core has a plurality of permeable cores disposed about a periphery of the external coil. In some embodiments, the plurality of permeable cores include four permeable cores disposed and equally spaced about the periphery of the external coil. In some embodiments, the corresponding permeable coils are disposed and equally spaced about the periphery of the internal coil. In some embodiments, a number of corresponding permeable coils is four. In some embodiments, the windings of the internal coil are wound about each corresponding permeable core so that the corresponding permeable cores are in electrical series. In some embodiments, the windings of the external coil are wound about each permeable core of the first set of permeable cores in electrical series. In some embodiments, a material of the permeable cores of the first set and the corresponding permeable cores is chosen to achieve a target field strength.

According to yet another aspect, a method of manufacture of a TETS is provided. The method includes disposing a first set of at least one permeable core in proximity to an external coil, and winding each of the first set of at least one permeable core by windings of the external coil; and for each permeable core disposed in proximity to the external coil, disposing a corresponding permeable core in proximity to an internal coil, and winding each corresponding permeable core by windings of the internal coil.

According to this aspect, in some embodiments, the first set of at least one permeable core includes a permeable core disposed at a center of the windings of the external coil. In some embodiments, a permeable core corresponding to the permeable core disposed at the center of the windings of the external coil is disposed at a center of the windings of the internal coil. In some embodiments, the first set of at least one permeable core has a plurality of permeable cores disposed about a periphery of the external coil. In some embodiments, the plurality of permeable cores include four permeable cores disposed and equally spaced about the periphery of the external coil. In some embodiments, the corresponding permeable coils are disposed and equally spaced about the periphery of the internal coil. In some embodiments, a number of corresponding permeable coils is four. In some embodiments, the windings of the internal coil are wound about each corresponding permeable core so that the corresponding permeable cores are in electrical series. In some embodiments, the windings of the external coil are wound about each permeable core of the first set of permeable cores in electrical series. In some embodiments, a material of the permeable cores of the first set and the corresponding permeable cores is chosen to achieve a target field strength. In some embodiments, the method further includes determining a current strength that is at least partially due to alignment between the external coil and the internal coil.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Some embodiments described herein are related to magnetic alignment of coils for transcutaneous energy transfer. In some embodiments, a permeable core 18A is placed at a center of the i-coil 18 and a permeable core 20A is placed a center of the e-coil 20. In some embodiments, a plurality of permeable cores 18A are disposed about the periphery of the i-coil 18 and a plurality of permeable cores 20A are disposed about the periphery of the e-coil 20. When current flows through the windings of the coil, the permeable cores become magnetized, causing a magnetic attraction between i-coil 18 and e-coil 20.

The attractive force between the permeable cores may be adjusted based on permeability of the cores, the number of windings, and the current through the windings. The attractive force may be adjusted in order to optimize the attractive performance to accommodate sources of patient to patient variability such as implant depth, activity, patient comfort.

The efficiency of energy transfer, and potentially the quality of coil to coil data communication, is a function of the relative position of the two coils. The better aligned the coils are in terms of both the radial position and the axial separation, the better the performance generally is. Maintaining the position of the external coil relative to the internal coil across a wide range of patient types, implant positions, patient activities, power demand levels, etc., may be needed for continuous operation of effective energy transfer. External straps and/or garments can be one mechanism to maintain coil alignment, but these methods may be cumbersome and burdensome for the patient to manage and maintain. Utilizing electromagnetic alignment of the coils provides an automatic mechanism to align and stabilize the external coil in the correct position.

Figure 1:
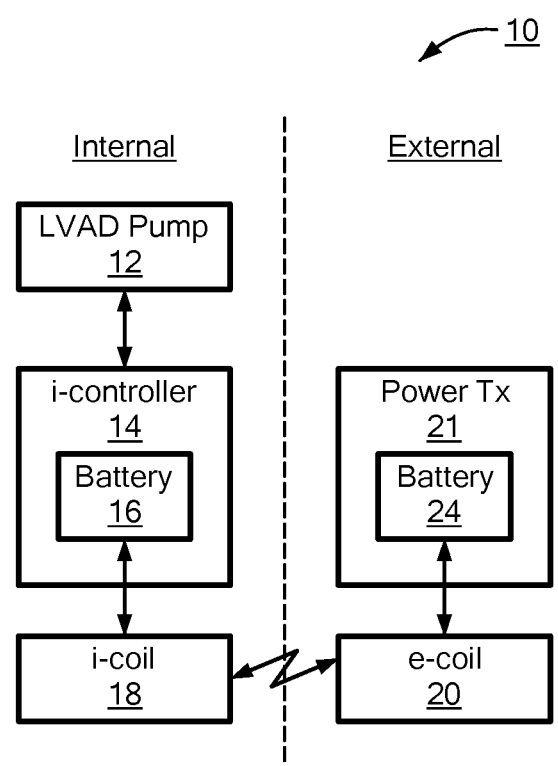
FIG. 1 is a block diagram of an implantable LVAD system.
Figure 2:
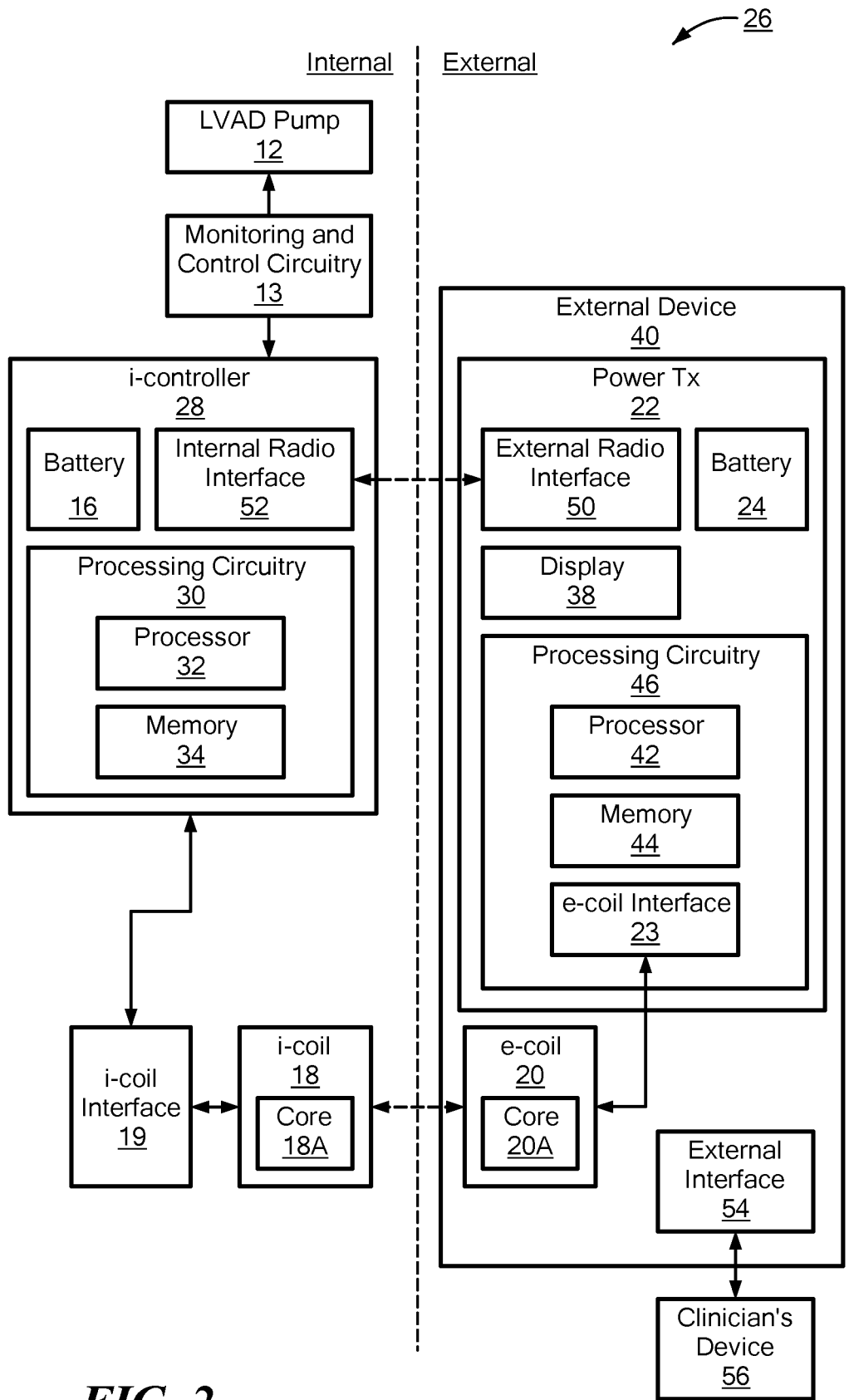
FIG. 2 is a block diagram of an embodiment of an LVAD system that implements magnetic alignment of coils for transcutaneous energy transfer.

FIG. 2 shows a block diagram of one example configuration of an implanted medical device system 26 having external components such as an external power transmitter 22, and internal components such as an internal controller (i-controller) 28 configured to perform functions described herein. As used herein, the term "implanted medical device system 26" refers to the system that includes both the implanted/implantable components as well as external components described herein.

The i-controller 28 may have processing circuitry 30 which may include a processor 32 and an internal memory 34. The processor 32 may be configured to execute computer instructions stored in the internal memory 34. Those instructions may include instructions to cause the processor to perform some of the processes described in more detail below.

A message or result from the i-controller 28 may be transferred from the i-controller 28 to an external display 38 of an external device 40, which may include a processor 42 and a memory 44 within processing circuitry 46, the external power transmitter 22 and the detachable battery 24, as well as the e-coil 20 in some embodiments. The memory 44 may be configured to store computer instructions to be executed by the processor 42. The external display 38 may be configured to display information received from the i-controller 28.

Electrical communication of signals and power between the internal components of i-controller 28 may be via communication busses and individual electrical conductors not shown in FIG. 2. For example, a multi-conductor address bus and data bus may connect processor 32 with internal memory 34. In some embodiments, an i-coil interface 19 associated with i-coil 18 may be included in the set of internal components making up the implanted medical device system 26. One purpose of i-coil interface 19 may be to modulate the alternating current applied to the i-coil 18 with signals from the i-controller 28 to be transmitted from the i-coil 18 to the e-coil 20 and/or to demodulate signals to be received by the i-coil 18 from the e-coil 20. In some embodiments, a purpose of the i-coil interface 19 is to provide conversion between the alternating current (AC) of the i-coil 18 and direct current (DC) to charge the battery 16.

The power supplied to the i-coil 18 may be adjusted by varying the AC electrical current in the e-coil 20. Some or all functions of the i-coil interface 19 may be included in the i-controller 28 and/or the i-coil 18. In some embodiments, the i-coil 18 and/or i-coil interface 19 may be internal to or considered part of the internal controller 28. Similarly, electrical communication of signals and power between the internal components of external device may be by communication busses and individual electrical conductors not shown in FIG. 2. For example, a multi-conductor address bus and data bus may connect processor 42 with memory 44.

In some embodiments, an e-coil interface 23 associated with e-coil 20 may be included in the set of external components making up the implanted medical device system 26. The e-coil interface 23 may include a TETS interface configured to demodulate information signals from the processing circuitry 30 transmitted from the i-coil 18 to the e-coil 20. The e-coil interface 23 may also be configured to couple power from the external power transmitter 22 to the e-coil 20. In some embodiments, the e-coil interface 23 may be two distinct units, one unit for demodulation of signals from the i-controller that are uploaded via the coils 18 and 20, and one unit for coupling power from the external power transmitter 22 to the e-coil 20. In some embodiments, the i-controller 28 may upload information to the external power transmitter 22 via the coils 18 and 20, but the power transmitter does not download information to the i-controller 28 via the coils 18 and 20.

In some embodiments, the internal components of the implanted medical device system 26 may include monitoring and control circuitry 13. A purpose of monitoring and control circuitry 13 may include monitoring speed and temperature, for example, of the LVAD pump 12. Another purpose of the monitoring and control circuitry 13 may include controlling the speed of the LVAD pump 12. In some embodiments, some or all of the monitoring and control circuitry 13 may be incorporated into the LVAD pump 12 and/or the i-controller 28. In some embodiments, some or all of the functions performed by the monitoring and control circuitry 13 may be performed by the processing circuitry 30. Thus, in some embodiments, the monitoring and control circuitry 13 may include one or more temperature sensors embedded in the LVAD pump 12. Information obtained from and/or about the LVAD pump 12, such as speed and temperature, may be sent to the external device 40 to be displayed by external display 38.

The various internal components making up the LVAD system may be grouped into one or more separate housings. Similarly, the various external components making up the LVAD system may be grouped into one or more separate housings. Further, some of the components shown and described as being internal to the i-controller 28 may be instead, external to i-controller 28 in some embodiments. Similarly, some of the components shown and described as being internal to the external device 40 may be instead, external to external device 40, in some embodiments. Note further that some of the functions performed by processor 32 may be performed instead by processor 42.

Note that transfer of information from the external device 40 to the internal memory 34, and vice versa, may be by wireless radio frequency (RF) transmission (over the air and through the body when the i-controller 28 is implanted). Accordingly, in some embodiments, the external device 40 includes an external radio interface 50 and the i-controller 28 includes an internal radio interface 52. In some embodiments, the external radio interface 50 and the internal radio interface 52 are RF transceivers having both an RF receiver for receiving information wirelessly and an RF transmitter for transmitting information wirelessly. Such RF transceivers may be Bluetooth and/or Wi-Fi compliant, for example. In some embodiments, the RF receiver and RF transmitter within the external device 40 or within the i-controller 28 are integrated into one unit, whereas in some embodiments, they could be physically separate units.

Also, information may be communicated to the i-controller 28 from the external power transmitter 22 via the coils 18 and 20, by modulating a parameter of power transmission, such as modulating the frequency of the transmitted power, or by modulating a parameter of the i-coil interface 19, for example, by modulating a tuning capacitance of the i-coil interface 19 or by modulating the load level of the i-controller and/or the i-coil interface 19.

The external device 40 could be a patient's external device that has an external interface 54 which provides an interface between the external device 40 and a clinician's device 56. The clinician's device might, for example, have a USB port and interface 54 might include a USB port, so that a USB cable may connect the two ports. The clinician's device 56 may read data from the external device 40 and write information and control signaling to the external device 40, in some embodiments. In the alternative to a wireline connection, the interface 54 could include or be a radio interface.

Figure 3:
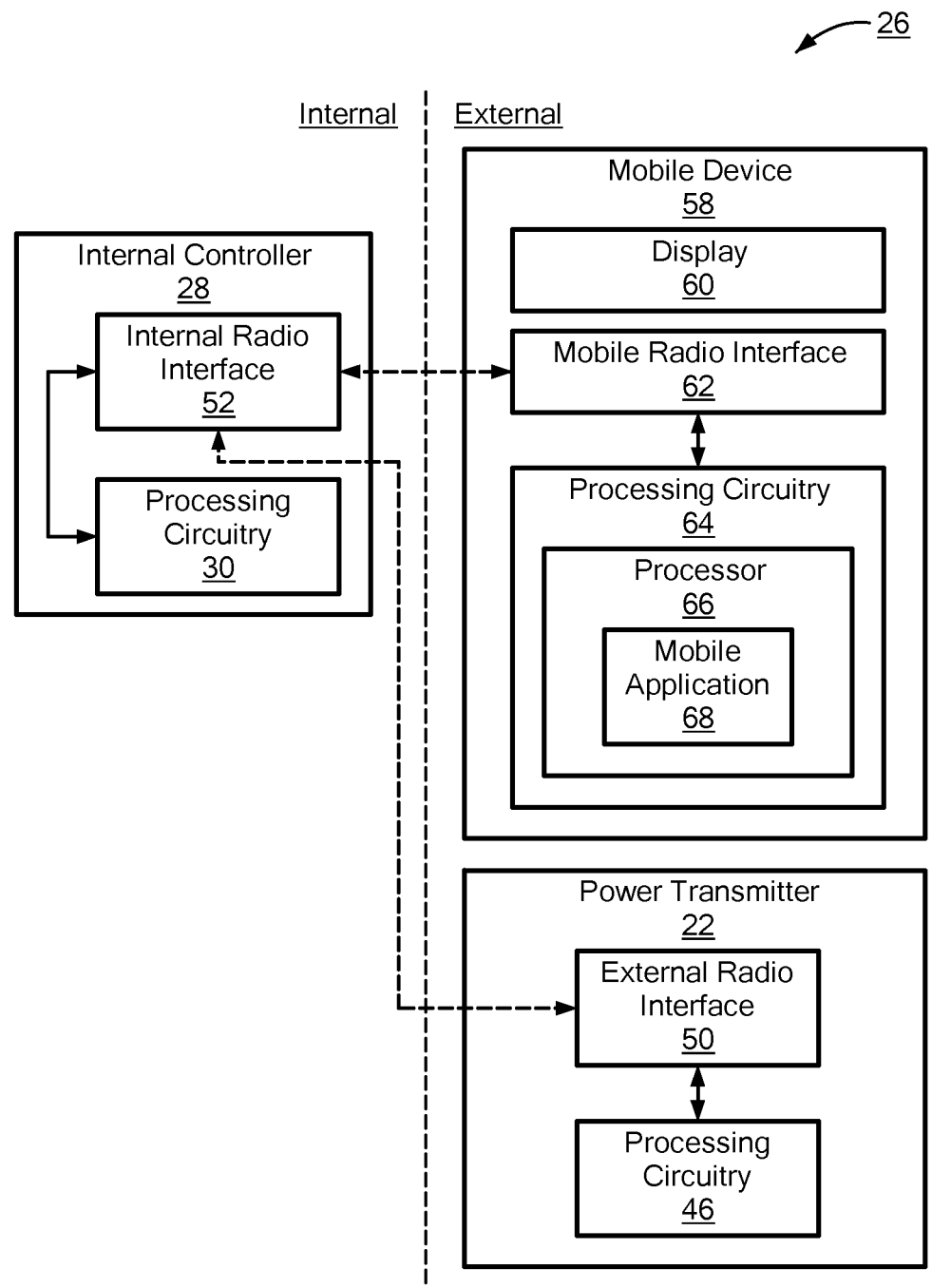
FIG. 3 is a block diagram of an implanted medical device system that includes a mobile device with a mobile application in wireless communication with an internal controller of the implanted medical device.

FIG. 3 is a block diagram of an implanted medical device system 26 that includes a mobile device 58 with a mobile application 68 in wireless communication with the i-controller 28. The mobile device 58 may be a mobile phone or other mobile digital device that can process information and communicate wirelessly with the i-controller. Accordingly, the mobile device 58 has a display 60, a mobile radio interface 62, processing circuitry 64, processor 66 which runs the mobile application 68. The radio interfaces 50, 52 and 62 may be Bluetooth Low Energy compatible radio interfaces, and the i-controller 28 may be a peripheral device responsible for advertising, while the mobile device 58 and the external power transmitter 22 may operate as master or central devices responsible for scanning and issuing connection requests.

Communication from the i-controller 28 to the external power transmitter 22 enables display on external display 38 of implanted device information such as pump data and alarm indications. The i-controller 28 may exchange, via the radio interfaces 50 and 52, diagnostic and log file data with the external power transmitter 22. The i-controller 28 may receive programming commands from an external device such as the clinician's device 56 or mobile device 58. Further, communication from the i-controller 28 to the mobile device 58, via the radio interfaces 52 and 62, enables remote monitoring in cases where the mobile device 58 is connected to the Internet, and enables the display 60 to display information about the state of the implanted portion of the implanted medical device system 26 such as, for example, remaining battery runtime. In some embodiments, the internal radio interface 52 may only communicate with the external radio interface 50 and the mobile radio interface 62 one at a time. In some embodiments, when the i-controller 28 is not engaged in a communication session with an external device, such as external power transmitter 22 or mobile device 58, the i-controller 28 may advertise continually to enable rapid reestablishment of the wireless connection between the i-controller 28 and the external power transmitter 22 or mobile device 58. Conversely, either one or both of the external power transmitter 22 or mobile device 58 may scan for such advertisements.

Figure 4:
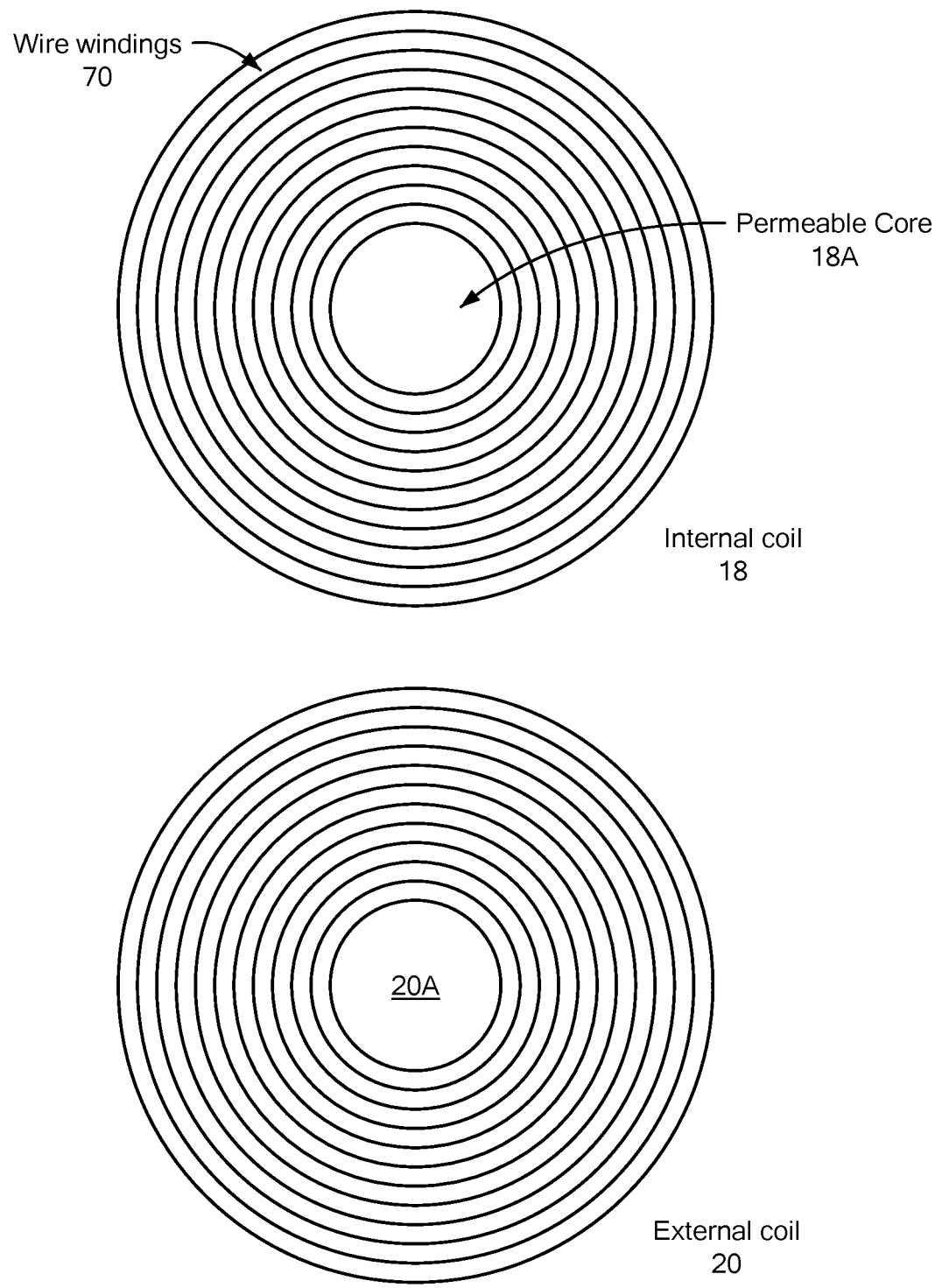
FIG. 4 is a diagram of a pair of coils with a permeable core at the center of each coil.

FIG. 4 is a diagram of a pair of coils 18 and 20 with a permeable core 18A, 20A at the center of each coil 18, 20, respectively. The permeable cores are wound by windings of their respective coils. When current flows through the coils 18 and 20, the permeable cores become magnetized and attract each other.

Figure 5:
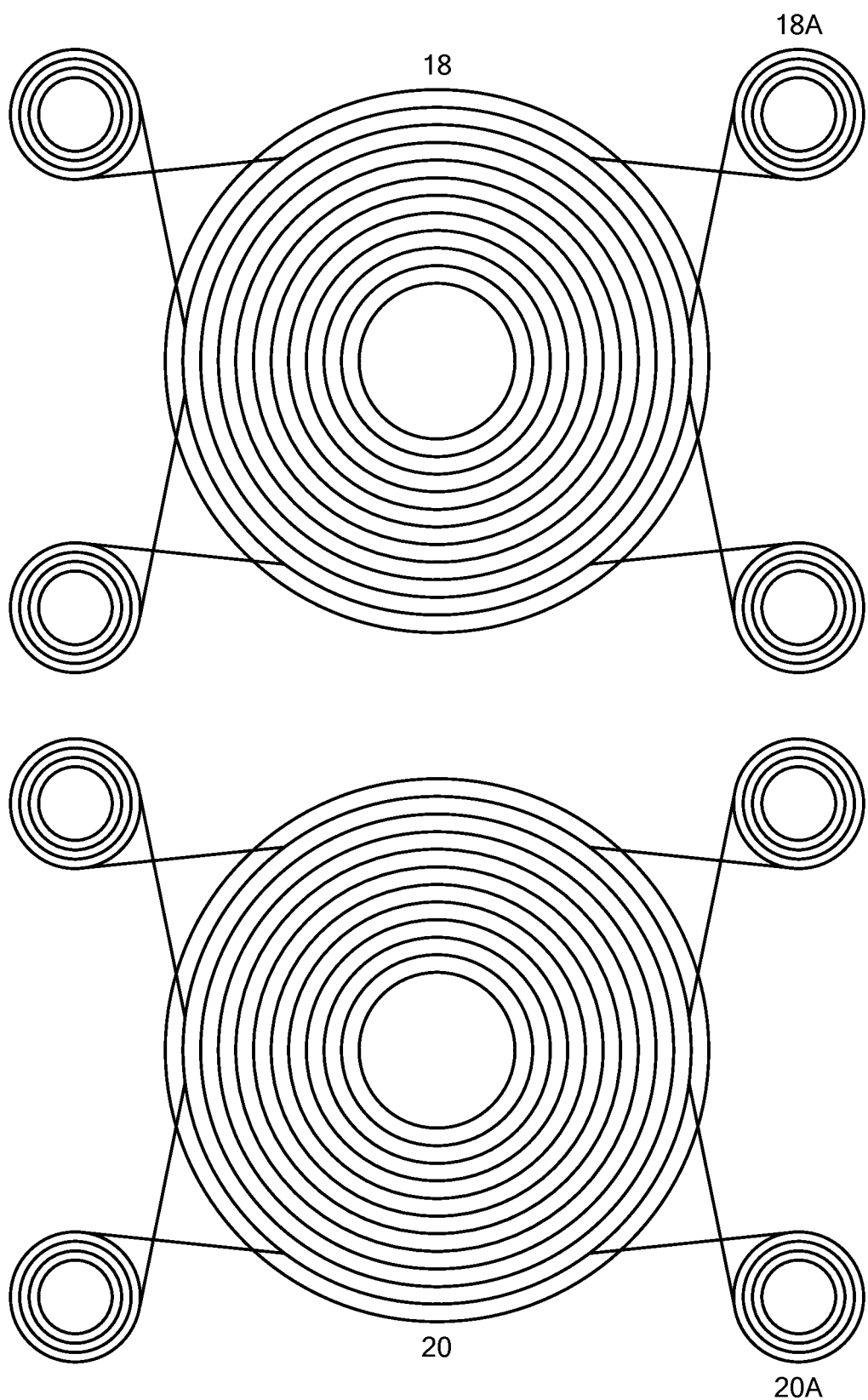
FIG. 5 is a diagram of a pair of coils with permeable cores disposed about the periphery of each coil.

FIG. 5 is a diagram of a pair of coils 18 and 20 with permeable cores 18A and 18B disposed about the periphery of each coil 18, 20. The permeable cores are wound by windings of their respective coils. When current flows through the coils 18 and 20, the permeable cores become magnetized and attract each other.

Note that too much attractive force can cause pain and discomfort to the patient due to potential squeezing or pinching. Too little attractive force can result in instability in the connection between the i-coil 18 and e-coil 20. The attractive force can be adjusted or optimized by the choice of materials for the permeable core 18A, 20A, number of windings near the permeable core 18A, 20A, and the magnitude of current flowing through the windings. The optimization can be performed at a time of design and manufacture to apply broadly to a patient population and expected implant depth. Alternatively, options can be provided to tailor the attractive force to the implant depth, activity of the patient, and comfort level, for example. As another alternative, the permeable core 20A of the e-coil 20 may be replaceable with cores of different permeability to achieve a different attractive strength for different patients and different activities. In some embodiments, the attractive strength may be controlled by the patient by a setting of a target strength corresponding to a target current. While the current flowing through the e-coil 20 may vary depending on a load placed on the e-coil 20 by the internal circuitry, the current will also depend on the alignment between the i-coil 18 and the e-coil 20. As the alignment increases, the current flowing through the e-coil 20 increases. Conversely, as the alignment decreases, the current flowing through the e-coil 20 decreases. In some embodiments, the patient may be able to select from a high, medium or low setting; a high setting causing the most current to flow through the windings about the permeable cores; a low setting causing the least current to flow through the windings about the permeable cores.

Figure 6:
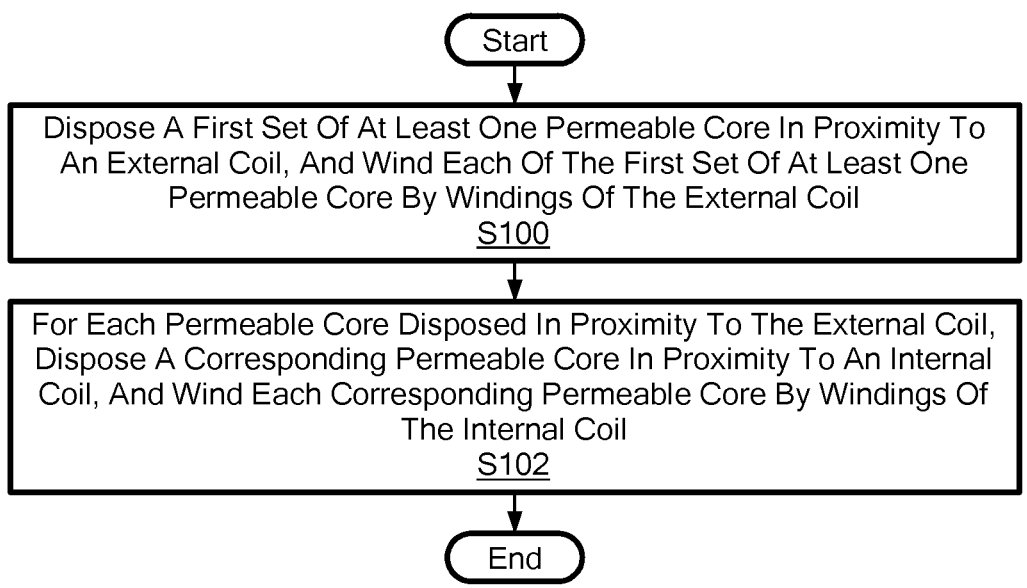
FIG. 6 is a flowchart of a process for creating magnetizable coils according to principles set forth herein.

FIG. 6 is a flowchart of a process for creating magnetizable coils according to principles set forth herein. The process includes disposing a first set of at least one permeable core 20A in proximity to an external coil 20, and winding each of the first set of at least one permeable core 20A by windings 70 of the external coil 20 (Block S100). The process further includes, for each permeable core 20A disposed in proximity to the external coil, disposing a corresponding permeable core 18A in proximity to an internal coil 18, and winding each corresponding permeable core 18A by windings of the internal coil 18 (Block S102).

According to one aspect, a TETS is provided that includes an external coil 20 having disposed in proximity thereto, a first set of at least one permeable core 20A that is wound by windings 70 of the external coil 20; and an internal coil 18 having disposed in proximity thereto, for each permeable core 20A disposed in proximity to the external coil 20, a corresponding permeable core 18A that is wound by windings 70 of the internal coil 18.

According to this aspect, in some embodiments, the first set of at least one permeable core includes a permeable core disposed at a center of the windings 70 of the external coil 20. In some embodiments, a permeable core corresponding to the permeable cored disposed at the center of the windings 70 of the external coil 20 is disposed at a center of the windings 70 of the internal coil 18. In some embodiments, the first set of at least one permeable core has a plurality of permeable cores disposed about a periphery of the external coil 20. In some embodiments, the plurality of permeable cores include four permeable cores disposed and equally spaced about the periphery of the external coil 20. In some embodiments, the corresponding permeable coils are disposed and equally spaced about the periphery of the internal coil 18. In some embodiments, a number of corresponding permeable coils is four. In some embodiments, the windings 70 of the internal coil 18 are wound about each corresponding permeable core so that the corresponding permeable cores are in electrical series. In some embodiments, the windings 70 of the external coil 20 are wound about each permeable core of the first set of permeable cores in electrical series. In some embodiments, a material of the permeable cores of the first set and the corresponding permeable cores is chosen to achieve a target field strength. In some embodiments, the TETS further includes processing circuitry 46 configured to determine a target current strength that is at least partially due to alignment between the external coil 20 and the internal coil 18.

According to yet another aspect, a method of manufacture of a TETS is provided. The method includes disposing a first set of at least one permeable core 20A in proximity to an external coil 20, and winding each of the first set of at least one permeable core 20A by windings 70 of the external coil 20; and for each permeable core 20A disposed in proximity to the external coil 20, disposing a corresponding permeable core 18A in proximity to an internal coil 18, and winding each corresponding permeable core 18A by windings 70 of the internal coil 18.

According to this aspect, in some embodiments, the first set of at least one permeable core includes a permeable core disposed at a center of the windings 70 of the external coil 20. In some embodiments, a permeable core corresponding to the permeable cored disposed at the center of the windings 70 of the external coil 20 is disposed at a center of the windings 70 of the internal coil 18. In some embodiments, the first set of at least one permeable core has a plurality of permeable cores disposed about a periphery of the external coil 20. In some embodiments, the plurality of permeable cores include four permeable cores disposed and equally spaced about the periphery of the external coil 20. In some embodiments, the corresponding permeable coils are disposed and equally spaced about the periphery of the internal coil 18. In some embodiments, a number of corresponding permeable coils is four. In some embodiments, the windings 70 of the internal coil 18 are wound about each corresponding permeable core so that the corresponding permeable cores are in electrical series. In some embodiments, the windings 70 of the external coil 20 are wound about each permeable core of the first set of permeable cores in electrical series. In some embodiments, a material of the permeable cores of the first set and the corresponding permeable cores is chosen to achieve a target field strength. In some embodiments, the method further includes determining, via the processing circuitry 46 a target current strength that is at least partially due to alignment between the external coil 20 and the internal coil 18.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media and memory may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope of the following claims.

What is claimed is:

1. A transcutaneous energy transfer system (TETS), comprising:
    an external coil having disposed in proximity thereto, a first set of at least one permeable core that is wound by windings of the external coil;
    an internal coil having disposed in proximity thereto, for each permeable core disposed in proximity to the external coil, a corresponding permeable core that is wound by windings of the internal coil; and
    processing circuitry configured to:
      receive a user selection of a target strength setting from a plurality of target strength settings, wherein the target strength setting corresponds to a strength of a magnetic attraction between the external coil and the internal coil; and
      set a current strength for a current flowing through the windings of the external coil based on the target strength setting, the current strength controlling the strength of the magnetic attraction between the external coil and the internal coil.

2. The TETS of claim 1, wherein the first set of at least one permeable core includes a permeable core disposed at a center of the windings of the external coil.

3. The TETS of claim 2, wherein a permeable core corresponding to the permeable core disposed at the center of the windings of the external coil is disposed at a center of the windings of the internal coil.

4. The TETS of claim 1, wherein the first set of at least one permeable core has a plurality of permeable cores disposed about a periphery of the external coil.

5. The TETS of claim 4, wherein the plurality of permeable cores includes four permeable cores disposed and equally spaced about the periphery of the external coil.

6. The TETS of claim 5, wherein corresponding permeable cores are disposed and equally spaced about a periphery of the internal coil.

7. The TETS of claim 6, wherein a number of the corresponding permeable cores is four.

8. The TETS of claim 6, wherein the windings of the internal coil are wound about each of the corresponding permeable cores so that the corresponding permeable cores are in electrical series.

9. The TETS of claim 1, wherein the windings of the external coil are wound about each permeable core of the first set of at least one permeable core in electrical series.

10. The TETS of claim 1, wherein a material of the first set of at least one permeable core and the corresponding permeable core is chosen to achieve a target field strength.

11. The TETS of claim 1, wherein the processing circuitry is further configured to determine a target current strength that is at least partially due to alignment between the external coil and the internal coil.

12. The TETS of claim 1, wherein the plurality of target strength settings comprises:
    a first setting causing a first amount of the current to flow through the windings of the external coil;
    a second setting causing a second amount of the current to flow through the windings of the external coil; and
    a third setting causing a third amount of the current to flow through the windings of the external coil, wherein the first amount is greater than the second amount, and wherein the second amount is greater than the third amount.

13. A method for a transcutaneous energy transfer system (TETS), comprising:
    disposing a first set of at least one permeable core in proximity to an external coil, and winding each of the first set of at least one permeable core by windings of the external coil;
    for each permeable core disposed in proximity to the external coil, disposing a corresponding permeable core in proximity to an internal coil, and winding each corresponding permeable core by windings of the internal coil;
    receiving a user selection of a target strength setting from a plurality of target strength settings, wherein the target strength setting corresponds to a strength of a magnetic attraction between the external coil and the internal coil; and
    setting a current strength for a current flowing through the windings of the external coil based on the target strength setting, the current strength controlling the strength of the magnetic attraction between the external coil and the internal coil.

14. The method of claim 13, wherein the first set of at least one permeable core includes a permeable core disposed at a center of the windings of the external coil.

15. The method of claim 14, wherein a permeable core corresponding to the permeable cored disposed at the center of the windings of the external coil is disposed at a center of the windings of the internal coil.

16. The method of claim 13, wherein the first set of at least one permeable core has a plurality of permeable cores disposed about a periphery of the external coil.

17. The method of claim 16, wherein the plurality of permeable cores includes four permeable cores disposed and equally spaced about the periphery of the external coil.

18. The method of claim 17, wherein corresponding permeable cores are disposed and equally spaced about a periphery of the internal coil.

19. The method of claim 18, wherein a number of the corresponding permeable cores is four.

20. The method of claim 18, wherein the windings of the internal coil are wound about each of the corresponding permeable cores so that the corresponding permeable cores are in electrical series.

21. The method of claim 13, wherein the windings of the external coil are wound about each permeable core of the first set of at least one permeable core in electrical series.

22. The method of claim 13, wherein a material of the first set of at least one permeable core and the corresponding permeable core is chosen to achieve a target field strength.

23. The method of claim 13, further comprising determining a target current strength that is at least partially due to alignment between the external coil and the internal coil.

* * * * *